US010001443B2

(12) United States Patent
Gardner et al.

(10) Patent No.: US 10,001,443 B2
(45) Date of Patent: Jun. 19, 2018

(54) HEROIN DETECTION BY RAMAN SPECTROSCOPY FROM IMPURE COMPOSITIONS COMPRISING AN INTERFERING FLUORESCENT CONTAMINANT

(71) Applicant: Thermo Scientific Portable Analytical Instruments Inc., Tewksbury, MA (US)

(72) Inventors: Craig Morris Gardner, Belmont, MS (US); Michael Derek Hargreaves, Lawrence, MA (US); Peidong Wang, Carlisle, MA (US); Yu Shen, Waltham, MA (US)

(73) Assignee: Thermo Scientific Portable Analytical Instruments Inc., Tewksbury, MA (US)

( * ) Notice: Subject to any disclaimer, the term of this patent is extended or adjusted under 35 U.S.C. 154(b) by 128 days.

(21) Appl. No.: 14/996,725

(22) Filed: Jan. 15, 2016

(65) Prior Publication Data
US 2016/0131586 A1    May 12, 2016

Related U.S. Application Data

(63) Continuation of application No. 13/529,916, filed on Jun. 21, 2012, now Pat. No. 9,255,842.
(Continued)

(51) Int. Cl.
*G01J 3/44* (2006.01)
*G01N 21/65* (2006.01)
(Continued)

(52) U.S. Cl.
CPC .............. *G01N 21/658* (2013.01); *G01J 3/44* (2013.01); *G01N 21/94* (2013.01);
(Continued)

(58) Field of Classification Search
CPC ............ G01J 3/44; G01N 21/65; G01N 21/64
See application file for complete search history.

(56) References Cited

U.S. PATENT DOCUMENTS

| 6,558,956 B1 | 5/2003 | Carron et al. |
| 6,574,501 B2 | 6/2003 | Lambert et al. |
| (Continued) | | |

FOREIGN PATENT DOCUMENTS

| CN | 2065607 U | 11/1990 |
| CN | 2246636 Y | 2/1997 |
| (Continued) | | |

OTHER PUBLICATIONS

Anger et al., "Enhancement and Quenching of Single-Molecule Fluorescence," Physical Review Letters, PRL 97, 113002 (2006).
(Continued)

*Primary Examiner* — Abdullahi Nur
(74) *Attorney, Agent, or Firm* — William R. McCarthy, III

(57) ABSTRACT

A method of identifying the presence of heroin in an impure heroin composition which contains heroin and at least one fluorescent contaminant which interferes with a Raman signal from the heroin. The method may include contacting the mixture with a solvent such as an alcohol, then contacting the resulting alcohol composition with a SERS surface. The surface may then be exposed to laser light from a hand-held Raman spectrometer to detect a Raman signal from the heroin. An apparatus for performing the method is also provided.

27 Claims, 13 Drawing Sheets

Related U.S. Application Data

(60) Provisional application No. 61/507,547, filed on Jul. 13, 2011, provisional application No. 61/508,519, filed on Jul. 15, 2011.

(51) Int. Cl.
*G01N 21/94* (2006.01)
*G01N 33/94* (2006.01)
*G01N 21/84* (2006.01)
*G01N 21/64* (2006.01)

(52) U.S. Cl.
CPC ......... *G01N 33/9486* (2013.01); *G01N 21/65* (2013.01); *G01N 21/8483* (2013.01); *G01N 2021/646* (2013.01); *G01N 2021/656* (2013.01); *G01N 2201/0221* (2013.01); *G01N 2201/06113* (2013.01)

(56) References Cited

U.S. PATENT DOCUMENTS

| | | |
|---|---|---|
| 6,770,488 B1 | 8/2004 | Carron et al. |
| 7,022,288 B1 | 4/2006 | Boss |
| 7,283,228 B2 | 10/2007 | Zhang et al. |
| 7,688,440 B2 | 3/2010 | Clarke et al. |
| 7,867,770 B2 | 1/2011 | Premasiri |
| 8,031,335 B2 | 10/2011 | Wang et al. |
| 8,081,308 B2 | 12/2011 | Wang et al. |
| 8,213,007 B2 | 7/2012 | Wang et al. |
| 8,467,052 B1 | 6/2013 | Chao et al. |
| 8,828,729 B1 | 9/2014 | Natan et al. |
| 2003/0185774 A1 | 10/2003 | Dobbs et al. |
| 2005/0170522 A1* | 8/2005 | Samsoondar ........... B01L 3/508 436/169 |
| 2005/0248758 A1 | 11/2005 | Carron et al. |
| 2005/0255236 A1 | 11/2005 | Deng et al. |
| 2006/0038979 A1 | 2/2006 | Natan et al. |
| 2006/0252965 A1 | 11/2006 | Flowers et al. |
| 2007/0155020 A1 | 7/2007 | Su et al. |
| 2010/0040979 A1 | 2/2010 | Weimer |
| 2010/0051801 A1 | 3/2010 | Erfurth et al. |
| 2010/0190661 A1 | 7/2010 | Lee et al. |
| 2011/0218218 A1 | 9/2011 | Aberg et al. |
| 2012/0242987 A1 | 9/2012 | Liu et al. |
| 2013/0206976 A1 | 8/2013 | Verbeck, IV |

FOREIGN PATENT DOCUMENTS

| | | |
|---|---|---|
| CN | 2495580 Y | 6/2002 |
| CN | 201222037 Y | 4/2009 |
| EP | 1595120 B1 | 12/2009 |
| JP | 638535 A | 1/1988 |
| WO | WO2011029888 A1 | 3/2011 |

OTHER PUBLICATIONS

Carter et al., "Raman Spectroscopy for the in Situ Identificaiton of Cocaine and Selected Adulterants," Applied Spectroscopy, 54(12), 1876-1881 (2000).

Rana et al., "Surface-enhanced Raman Spectroscopy for Trace Identification of Controlled Substances: Morphine, Codeine, and Hydrocodone," J of Forensic Sciences, 56(1), 200-207 (2011).

Sagmuller et al., "Application of SERS Spectroscopy to the Identification of (3,4-methylenedioxy)amphetamine in Forensic Samples Utilizing Matrix Stabilized Silver Halides," Analyst, 126, 2066-2071 (2001).

Sengupta et al., "Bioaerosol characterization by surface-enhanced Raman spectroscopy (SERS)," J of Aerosol Science, 36 (2005) 651-664.

Zhao et al., "Detecting of Trace Contraband Cocaine, Heroin and Caffeine on Aluminum Surface by Micro Raman with Excitation Light 514.5nm," 160-161.

\* cited by examiner

Raman spectrum - Heroin street sample

HEROIN DETECTION BY RAMAN SPECTROSCOPY FROM IMPURE COMPOSITIONS COMPRISING AN INTERFERING FLUORESCENT CONTAMINANT

CROSS-REFERENCE TO RELATED APPLICATIONS

This application is a continuation of U.S. patent application Ser. No. 13/529,916, filed Jun. 21, 2012, and claims priority to U.S. provisional patent application Ser. No. 61/507,547, filed Jul. 13, 2011 and U.S. provisional patent application Ser. No. 61/508,519, filed Jul. 15, 2011, all entitled "Heroin Detection by Raman Spectroscopy from Impure Compositions Comprising an Interfering Fluorescent Contaminant" and are incorporated herein by reference in their entireties.

FIELD

This invention generally relates to detecting the presence of heroin by Raman spectroscopy, in an impure composition which may include a contaminant which would normally interfere with a Raman signal from the heroin.

BACKGROUND

Raman spectroscopy is an effective tool for identifying and characterizing a vast array of substances. In Raman spectroscopy, light typically from a laser and of a known wavelength (typically infrared or near infrared) is directed at a specimen. The laser light (also sometimes referred to as the Raman pump) interacts with the electron clouds in the molecules of the specimen and, as a result of this interaction, experiences selected wavelength shifting. The precise nature of this wavelength shifting depends upon the materials present in the specimen. A unique wavelength signature (typically called the Raman signature) is produced by each specimen. This unique Raman signature permits the specimen to be identified and characterized. More specifically, the spectrum of light returning from the specimen is analyzed with a spectrometer so as to identify the Raman-induced wavelength shifting in the Raman pump light, and then this wavelength signature is compared (e.g., by a computer) with a library of known Raman signatures, whereby to identify the precise nature of the specimen. Raman spectroscopy is widely used in scientific, commercial and public safety areas. Recent technological advances have made it possible to significantly reduce the size and cost of Raman spectroscopy systems. This has in turn increased the range of practical applications for Raman spectroscopy. For example, portable units have recently become available for various field uses, such as the on-site identification of potentially hazardous substances.

The interception of illegal drugs, such as heroin, has become a severe policing problem worldwide. It is difficult for law enforcement personnel in the field to at least initially identify any particular substance as likely being a prohibited one. This can lead to false arrests or releasing suspects who are indeed carrying such illegal drugs. While a properly equipped lab can make a definitive analysis, typical lab equipment does not lend itself to use by law enforcement personnel in the field because it is either too heavy, cumbersome, difficult to operate, or too expensive to distribute widely to large numbers of law enforcement personnel.

SUMMARY

It would be desirable then to provide an instrument and method for providing at least an initial detection of illegal drugs, such as heroin (diacetyl morphine), and which can be readily and economically distributed to a wide variety of law enforcement personnel for use in the field. That is, for use at locations outside or remote from a laboratory, and often adjacent where a suspect may be encountered, such as on a street or in a car.

The present invention realizes that while Raman spectroscopy in principle lends itself to identifying illegal drugs such as heroin, illegal heroin sold or used is in fact typically a heroin composition which can contain a variety of contaminants in addition to heroin. Some of these contaminants are "cutting agents", which are intentionally added to the heroin by dealers to increase its volume, such as caffeine, paracetamol, chloroquine, phenolphthalein, methaqualone, and mannitol. Another contaminant may be monacetyl morphine (typically 6-monoacetylmorphine) which results from heroin degradation after several weeks, particularly where the heroin has been stored in a moist environment or in non-acidified aqueous solutions. The present invention realizes that such contaminant compounds are often strongly fluorescent and can interfere with a Raman signal characteristic of heroin. In addition, illegal heroin may be the free diacetyl base or may be in the form of heroin hydrochloride, which itself is a mixture of the hydrochloride salt and the free diacetyl base form, further complicating the task of detecting heroin in the field.

The present invention then, provides in some embodiments a method and apparatus for detecting the presence of heroin in an impure heroin composition which contains heroin and at least one fluorescent contaminant which interferes with the Raman signal from the heroin. The method may include contacting the mixture with a solvent such as an alcohol, and particularly a volatile solvent such as ethanol, then contacting the resulting composition with a SERS surface. The SERS surface is then exposed to laser light from a hand-held Raman spectrometer and a Raman signal characteristic of the heroin is detected in the Raman spectrometer, such as the hand-held Raman spectrometer.

The present invention further provides in some embodiments an apparatus or kit which may be used in a method of the present invention. The apparatus or kit may be used for identifying the presence of heroin in an impure heroin composition containing heroin and at least one fluorescent contaminant as previously described. Such an apparatus or kit may comprise a container of an organic solvent such as a volatile organic solvent such as a volatile alcohol, and which may particularly be ethanol (for example, a vial or bottle of ethanol). A solvent may be tested for suitability with suitable surfaces and compositions to be tested, by comparing the results obtained under the same conditions but with a reference solvent. The apparatus or kit may comprise a SERS surface to receive an ethanol or other composition resulting from contact of the ethanol or other organic solvent with the impure heroin composition. The apparatus or kit may also comprise an elongated test member as described, which may carry the SERS surface. The foregoing components can be combined in any combination of two or more, or all, as part of the apparatus or kit, optionally together with a hand-held spectrometer disclosed herein.

Computer program products are further provided, and may include any computer program product carrying a computer program which can execute any method of the present invention. A computer program "product" is a tangible, non-transitory medium, which may carry a computer program of the present invention (for example, a magnetic, optical, or solid-state memory) in a non-transitory, but potentially temporary, form.

The present invention also provides a Raman spectrometer, with a light source to direct light to a surface, and a spectrograph to acquire a Raman spectrum from the surface. The spectrometer further includes a processor which can carry out any of the methods of the present invention. For example, the processor may compare a Raman spectrum of the surface without the presence of a component thereon, with one or more criteria in a memory and identifies the surface as one which is or is not suitable for testing for the presence of a component. The processor may also compares the Raman spectrum of the surface with a composition thereon to be tested for the component with one or more criteria in a memory to test for the presence of the component. The processor may also provide an indication to a user that the surface is or is not suitable, such as by an audible and/or visible alert.

BRIEF DESCRIPTION OF THE DRAWINGS

Embodiments of the invention will now be described in which.

DETAILED DESCRIPTION OF EMBODIMENTS OF THE INVENTION

Figure 1:
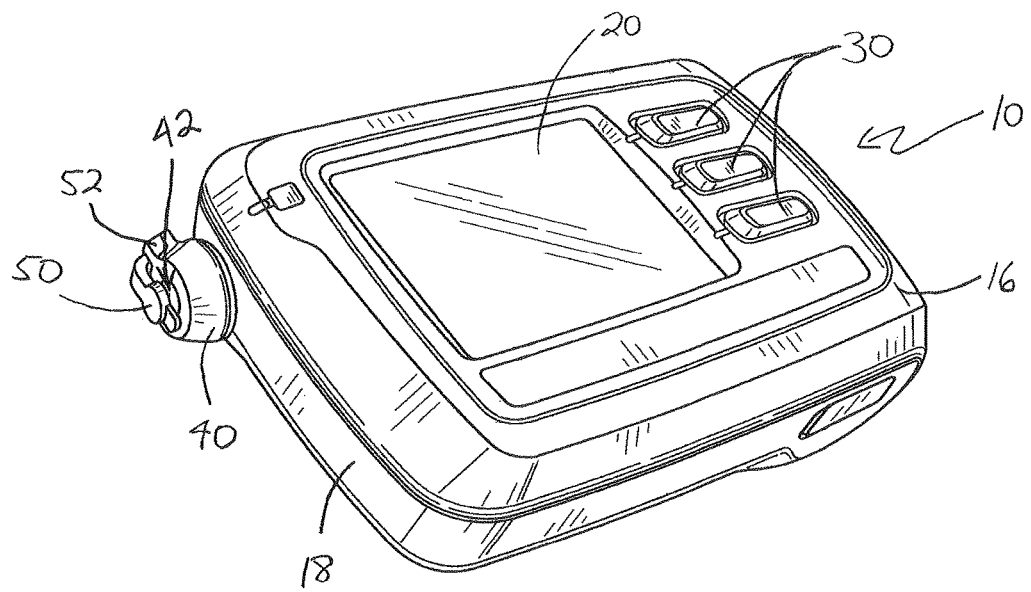
FIG. 1 is a top perspective view of a portable Raman spectrometer used in embodiments of the present invention.
Figure 2:
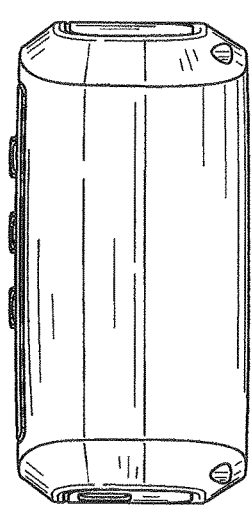
FIGS. 2 and 3 are opposite end views of the Raman spectrometer of FIG. 1.

Embodiments of the invention provide a method of identifying the presence of heroin in an impure heroin composition which contains heroin and at least one fluorescent contaminant which interferes with the Raman signal from the heroin. The amount of heroin contained in the sample can range from as low as 2%, 10%, 30% or 50% to any of 60%, 70%, 80% or even 100%. These percentages and any other percentage herein unless specifically mentioned otherwise, are weight percentages. By "heroin" in this context is meant heroin in any form, whether the hydrochloride or other salt, or the free base (that is, no or substantially no salt form is present). Various types of fluorescent contaminants have been described above. The amount of such contaminants which may be present may range from any of 1%, 5%, 10%, 30%, 50%, 95% or more. These interfere with a Raman signal from the heroin by producing a broad emission across wavelengths that overlaps in whole or in part with any part of the Raman spectrum being used to identify the presence of heroin. For example, a Raman spectrum used to characterize heroin might be anywhere within the wavenumber range of 250 to 3200 $cm^{-1}$, or 500 to 2000 $cm^{-1}$, 300 to 1800 $cm^{-1}$, such as 600-650 $cm^{-1}$, or even 620-635 $cm^{-1}$. Then the fluorescence from a contaminant might interfere with that spectrum if it produces a substantial emission over all or any part of (for example, over 10, 20 or 30 $cm^{-1}$ range) that spectrum, and particularly if it produces such a substantial emission over the a range from any of 400, 500, or 550 $cm^{-1}$ to any of 600, 700, 800 or 1000 $cm^{-1}$. By "substantial" in this context may include reducing the signal/noise ratio under the same conditions of measurement without the fluorescence, by at least 5%, 10%, 30%, 50% or more. While processing of the detected Raman spectrum might be used to reduce the effect of background in specific situations, it does not function well since various cutting agents and other contaminants affect the fluorescence of the composition. In this application, all wavenumbers given with reference to Raman spectra are Raman shifts from the illuminating radiation wavelength unless a contrary indication is given. "Identifying" or "identifying the presence" or similar terms, includes either or both a qualitative evaluation (for example, the substance is or is not present) as well as a quantitative evaluate (that is, how much is present). By "suitable" is referenced that something (such as a surface) does not meet any predetermined criteria, such as not meeting predetermined performance criteria or criteria that indicates the surface is not authorized for use with a particular instrument. "May" in this application references something that is optional, for example if an item "may" be present then that means that item either is present or is not present. "Or" in this application references that either one, or both. For example, providing an indication a surface is or is not suitable, means providing an indication only when the surface is suitable, or providing an indication only when the surface is not suitable, as well as providing an indication of both suitable and unsuitable. A "processor" as used herein may be any hardware or hardware/software combination which is capable of carrying out the steps require of it. For example, a processor may be a suitably programmed microprocessor or application specific integrated circuit. A processor may also include a memory of any known type, such as a read-only or read-write memory, which holds instructions and data for spectrometer operation as described herein.

In embodiments of the method, the heroin composition is contacted with a solvent, such as a volatile solvent, and in particular a volatile alcohol such as ethanol. At least some small proportion of the sample may dissolve in the solvent as a result of the contacting step. The resulting composition is then contacted with a SERS surface. SERS is Surface Enhanced Raman Spectroscopy, and a SERS surface as used in this application refers to a surface which enhances the Raman spectrum of heroin over what would be observed under the same conditions absent the surface. For example, the average or peak Raman signal of heroin in some embodiments may be increased by any amount over the same composition without the surface over the region of interest, that is the wavelength or wavenumber range used to characterize the presence of heroin as described herein. In the case of the mixtures resulting from contact of the solvent with an impure heroin composition as described herein, the comparison would be the same resulting mixture as dried on the SERS surface versus the solution or a surface which is known to have no SERS activity. Such an increased signal amount could, for example, be at least 100% or, in some embodiments that signal may be increased by a factor of even at least 10 times, or 100 times, or 1000 times, or even by at least 10,000 times. One way to identify a suitable SERS surface is to check for the foregoing increased signal amount over the same conditions but without the SERS surface. SERS is a known phenomenon, the operation of which is described, for example, in U.S. Pat. No. 7,898,658, U.S. Pat. No. 7,880,876, U.S. Pat. No. 7,889,334, U.S. Pat. No. 7,867,770, U.S. Pat. No. 7,738,096 and elsewhere. These references, and all other references cited herein are incorporated into this application by reference, except to the extent to which they may conflict with the present application in which case the present application prevails.

Examples of SERS surfaces which may be used include gold, silver, or copper, or surfaces containing some percentage of them, for example at least 50%, 60%, 80% or 95%. The SERS surface may be a continuous surface. By a "continuous surface" in this context is referenced a continuous surface of at least 1 mm$^2$, 2 mm$^2$, 5 mm$^2$, 10 mm$^2$ or 20 mm$^2$ in continuous surface area. Alternatively a SERS surface can be non-continuous such as that provided by nanoparticles which may have diameters such as from 10 to 200 nm (or even 80 to 120 nm). Such a continuous SERS surface may be textured, that is not smooth. A textured continuous surface may be a randomly roughened surface. One way of forming such a continuous SERS surface is by depositing a thin layer of silver such as by electrochemical deposition or sputtering, onto a roughened silicon substrate so that it overlays and is in contact with the silicon substrate. As a result, if the layer is thin enough it will follow the rough contours of the substrate. The thickness of such a silver layer may be from 10, 20, 50, 100 nm or more to any of 200, 500, 1000 nm or more and may be deposited by any well known methods for depositing metal layers. By "roughened" in this context is referenced a continuous surface which has an RMS (root mean square) surface height variation of between 50 nm to 300 nm. Suitable roughened SERS surfaces of gold, silver, or copper for example, can be prepared by methods such as described by: Dwight et al., "Surface Enhanced Raman Spectroscopy for Detection of Toxic- and Marker-Chemicals: Ultra-Sensitive and Reproducible Substrates", NDIA Homeland Security Symposium, Arlington, Va., May 25-28, 2004; U.S. Pat. No. 7,450,227 and PCT patent publication WO/2006/137885 both titled "Surface Enhanced Raman Spectroscopy (SERS) Substrates Exhibiting Uniform High Enhancement and Stability".

The surface with the resulting alcohol composition can be exposed to laser light of sufficient intensity to generate a useful Raman signal. The alcohol may be evaporated from the SERS surface before exposure to the laser light simply as a result of evaporation at ambient temperature into the atmosphere. Alternatively, or in addition to such drying, the laser light itself if of sufficient intensity, may completely or partially evaporate the alcohol. For example, the laser light may evaporate at least 1%, 2%, 10%, 20%, 30%, 50% or 80% of the alcohol deposited on the SERS surface. A typical laser wavelength may be between about 500 nm to 900 nm, for example 785 nm. Laser intensity at the SERS surface may, for example, be between any of 50, 100, or 200 mW to any of 300, 400, 500 mW or more.

The Raman signal may be detected in a hand-held Raman spectrometer. By "hand-held" in this context is referenced a spectrometer instrument which weighs less than 10 kg, and more typically less than 5, 2, 1, or even less than 0.5 or 0.2 kg, and may have dimensions of less than 50 cm or 30 cm in each dimension, and one of the dimensions (the thickness) may even be less than 10 cm or 5 or 3 cm. A "hand-held" spectrometer will often be battery powered with the battery typically fitting within the foregoing dimensions and included in the foregoing weights, although a separate power supply could be provided and connected to the spectrometer.

The apparatus or kit for use in identifying the presence of heroin may include a container of the volatile organic solvent of any of the types previously described, such as ethanol. By "ethanol" or other "solvent" herein is meant a liquid which is at least 10%, 20%, 50%, 60%, 80% or 90% or more of the solvent (for example, 95% or 99% or more). The container may be any suitable container which retains the solvent and prevents evaporation over an extended period. By "prevents evaporation" in this context is referenced, for example, that no more than 10% or even no more than 5%, evaporates over a week, month, or year when stored, for example, at 20° C.

The present invention also contemplates a verification routine which may be used by itself or optionally in conjunction with other aspects of methods of the present invention. In this verification routine a Raman spectra from the previously unused SERS surface is used to identify the surface to the spectrometer as one which is suitable for detecting heroin, or matches a surface that is authorized to be used with the spectrometer for a test selected on the spectrometer by a user, or to determine if the surface may be contaminated and unfit for use. In this sub-routine the previously unused SERS surface is illuminated with the spectrometer laser and the resulting Raman spectrum collected and analyzed by the spectrometer to see if it meets with any predetermined criteria. If not, a visible and/or audible warning may be provided to the user indicating that the SERS surface or test strip on which it is carried, is not suitable for the selected test with the spectrometer. The matching determination may be based on any predetermined criteria from a reference SERS surface Raman spectra stored in memory and compared with the Raman spectra of a SERS surface in question.

The present invention further contemplates that the foregoing verification routine may be more generally used with any analytical instrument in different tests. In this event the SERS surface may be replaced by another suitable surface such as one which both functions to enhance identification of a component by the analytical instrument (such as an optical analytical instrument), but at the same time can function for the verification routine in its unused state. For example, the method may be a method of verifying a surface as suitable for use in enhancing the identification of a component in a test of a composition for the component on an analytical instrument. In this embodiment the method may include subjecting the surface to a measurement on the analytical instrument without the presence of the component on the surface, and collecting a result of the test. The collected result may be compared, for example in a processor, with one or more predetermined criteria stored in a memory. If the collected result meets the one or more predetermined criteria, then the surface is subjected to the test on the analytical instrument after exposure of the surface to the composition. Optionally, if the collected result does not meet the one or more predetermined criteria then a visible or audible warning may be provided to a user of the instrument indicating that the surface is not suitable for the test. As already mentioned, this method may be applied to testing for a suitable SERS surface.

The present invention also provides, alone or together in an apparatus or kit with any other components described herein, an elongated test member in the form of a test strip or wand. This member carries a test surface, such as a SERS surface, at a first end, and a second section at a second end opposite the first which section is displaced laterally from the first end. The second section is shaped such that the SERS surface can be placed against a port of a cone projecting from a side of a spectrometer while the second section lies alongside and against that spectrometer side. This can assist a user in retaining the SERS surface in position against the port during use. The present invention further provides a test member which may be elongated, and which carries a test surface, such as a SERS surface described herein, located in a depression in one end of the member. The depression may be dimensioned to fit snugly over an end of a projection (such as a nose cone of a spectrometer or other analytical instrument) so as to assist in holding the test surface in position adjacent a port located at an end of the projection (such as the nose cone). This depression configuration may be combined with the first end and second section configuration as just described. By "cone" in this application is referenced a projection of any shape extending away from a surface. The projection typically reduced in cross-section area moving away from the surface, and could be conical in shape (that is of circular cross-section of decreasing diameter moving away from the surface) but could be of many other shapes (for example, rectangular or ellipsoid in cross-section with our without reducing cross-section area moving away from the surface).

The present invention further provides a cover such as described herein, for a cone of an analytical instrument such as described herein and which carries a detection port. The cover has an inside surface which will can be used as a reference or calibration standard for the analytical instrument when the cover is closed.

Figure 3:
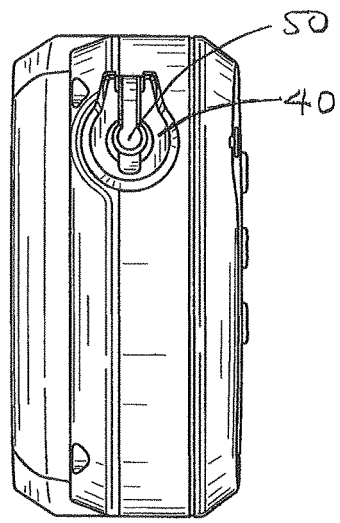
Figure 3B:
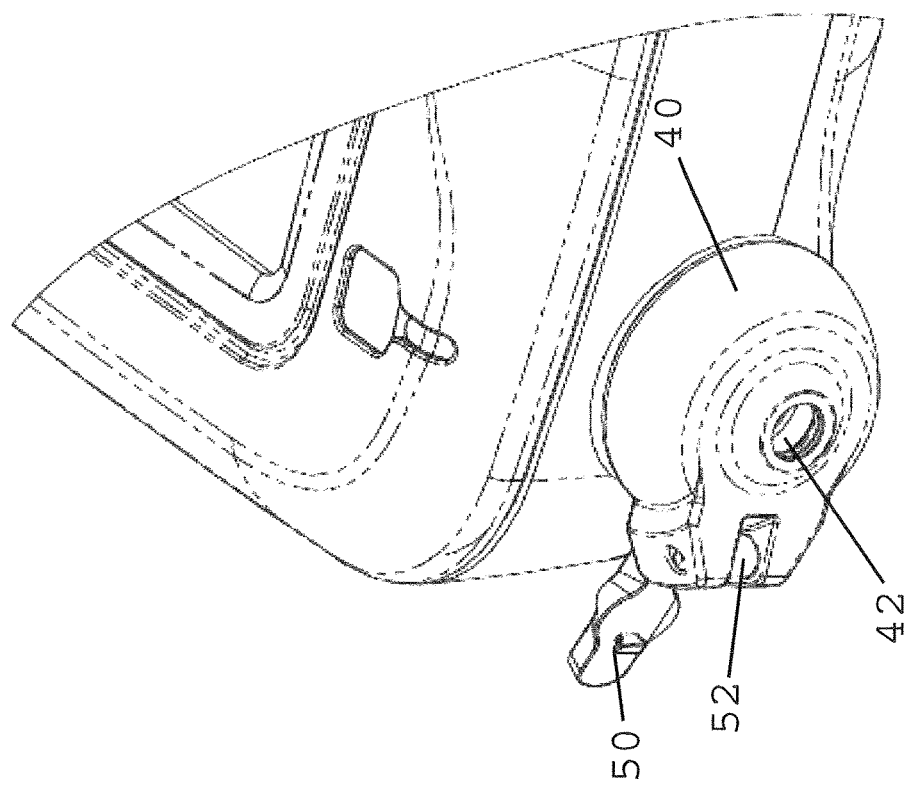
FIGS. 3A and 3B show a portion of the Raman spectrometer of FIG. 1, with the port cover closed in FIG. 3A and open in FIG. 3B.
Figure 3A:
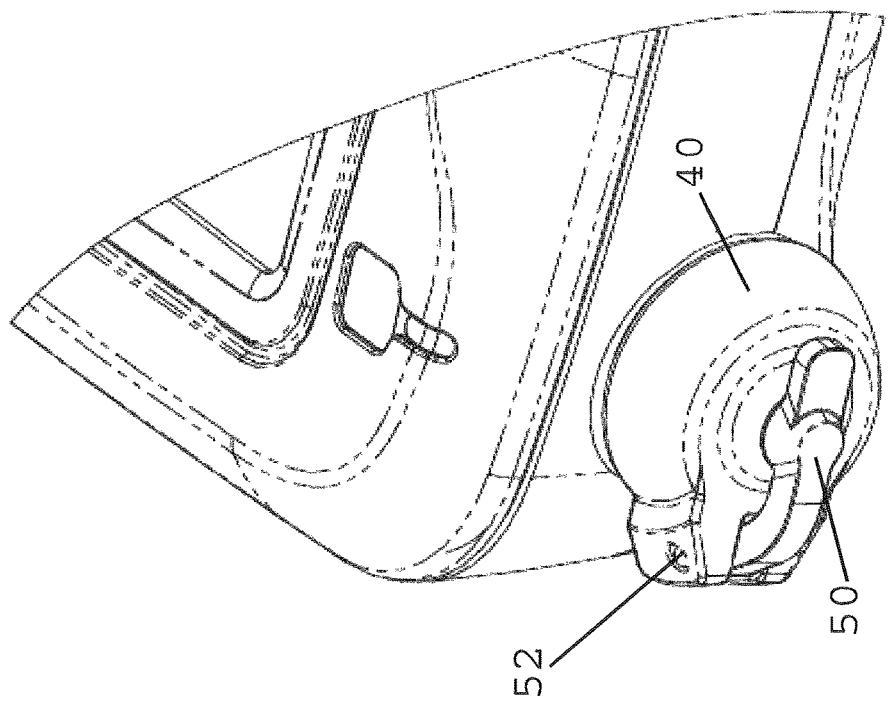

Referring now to FIGS. 1-7, some embodiments of different components of an apparatus or kit of the present invention are illustrated. FIG. 1 shows a perspective view of a hand-held Raman spectrometer 10 which includes a housing 16, user controls 30, and display screen 20 which displays user instructions and provides results on whether heroin is identified in a composition or not. Spectrometer 10 also includes a nose cone 40 which projects from a flat side 18 of housing 16 and has a port 42 at an end distal from side 18. In FIG. 1 port 42 is shown covered by a cover 50 in the form of a cap, mounted by a hinge 52 to housing 16 to reversibly swing between a position covering port 42 (as shown in FIGS. 1 and 3A) and a position uncovering port 42 (as shown in FIG. 3B). In the uncovered position a sample to be tested for the presence of a compound, in particular a SERS surface carrying a composition, can be positioned adjacent port 42 for testing. An inside of cover 50 can carry or be made of a material suitable for testing or calibrating the functioning of the spectrometer, such as polystyrene. In operation and with port 42 uncovered, laser light is emitted through port 42 onto a sample position against port 42, and the resulting detected Raman signal is received from the sample back through port 42 into housing 16.

Figure 4:
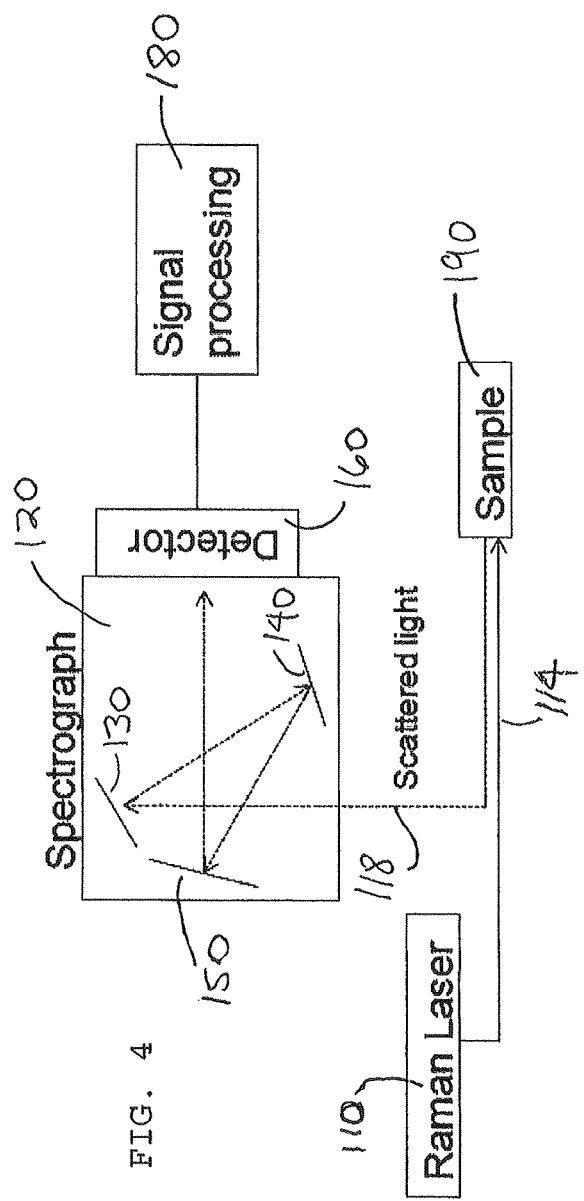
FIG. 4 is schematic diagram of the optics of the Raman spectrometer of FIG. 1.

Referring to FIG. 4, spectrometer 16 includes a Raman laser which emits light at, for example, 400 to 900 nm, or 700 to 850 nm, for example at 785 nm. The emitted laser light travels along optical path 114 within housing 16 and exits through end 42 when cover 50 is swung backward during testing of a sample composition 190. The resulting scattered light is detected back through end 42 and travels along path 118 within housing 116 and is directed by optical components 130-150 of a spectrograph 120 onto a detector 160 of spectrograph 120. The resulting Raman spectrum is detected by detector 160 and signal processing and/or digitizing is handled by signal processor 180. Processor 180 may be a suitably programmed microprocessor or application specific integrated circuit, and includes a read-only or read-write memory of any known type which holds instructions and data for spectrometer operation as described herein.

Figure 5:
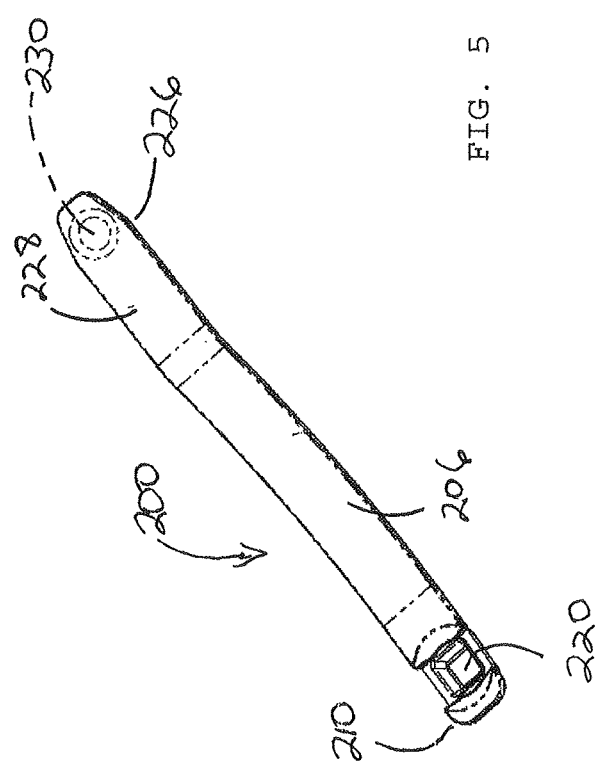
FIG. 5 is a perspective view of a SERS surface containing test strip used in embodiments of the present invention.
Figure 6:
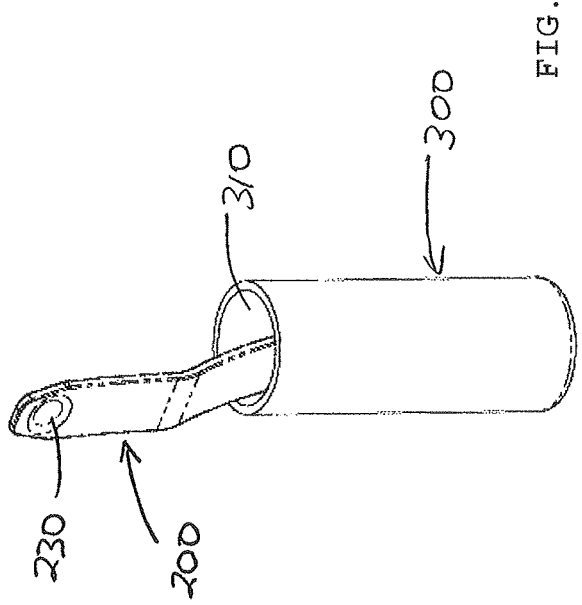
FIG. 6 is a perspective view of an embodiment of a solvent container and the SERS test strip of FIG. 5.

Referring to FIG. 5 the test strip 200 shown may be made of plastic and has a curved first section 206 and shorter flat second section 228. A first end 210 of strip 200 has a depression which carries a continuous SERS surface 220 facing in a first direction. The depression is dimensioned to fit snugly over an end of nose cone 40 so as to assist in holding surface 220 in position over port 42 as will be described. Second section 206 then is at a second end opposite the first and is displaced laterally (that is sideways to the longest dimension) from the first end. The second section is shaped such that the SERS surface can be placed against a port of a cone projecting from a side of a spectrometer while the second section lies alongside and against that spectrometer side. This can assist a user in retaining the SERS surface in position against the port during use as will be described. SERS surface 220 may be of any of the materials previously mentioned, such as a surface made from gold, silver, or copper, either substantially pure or of a composition previously described. As already mentioned SERS surface 220 may be roughened as a result of a thin layer of the surface material being deposited on a roughened substrate, such as a silicon substrate. The substrate may be attached to the remainder of the test strip by gluing or other adhesion methods, or molded or deposited directly onto the remainder of the strip. The degree of roughness may be as discussed above. A second end 226 of test strip 226 carries a depression facing in a second direction the opposite the first direction which SERS surface 220 faces. Depression 230 can be used for measuring a quantity of sample composition for testing as will be described.

An apparatus or kit of the present invention may include an elongated test member in the form of test strip 200 together with a container in the form of vial 300. Vial 300 may be glass or plastic and has an end 310 which may be sealed by a cap or other means (not shown) to prevent evaporation of a solvent contained within vial 300. The contained solvent may be a volatile organic solvent such as an alcohol (particularly ethanol), not shown. The apparatus or kit may optionally include the spectrometer 16. Any vial and test strip of the present invention can be shipped together in a same package with printed instructions on their use together and with a spectrometer such as spectrometer 16. Additionally, any such vial and test strip can be shipped together with a hand-held Raman spectrometer of a type already described.

Figure 14:
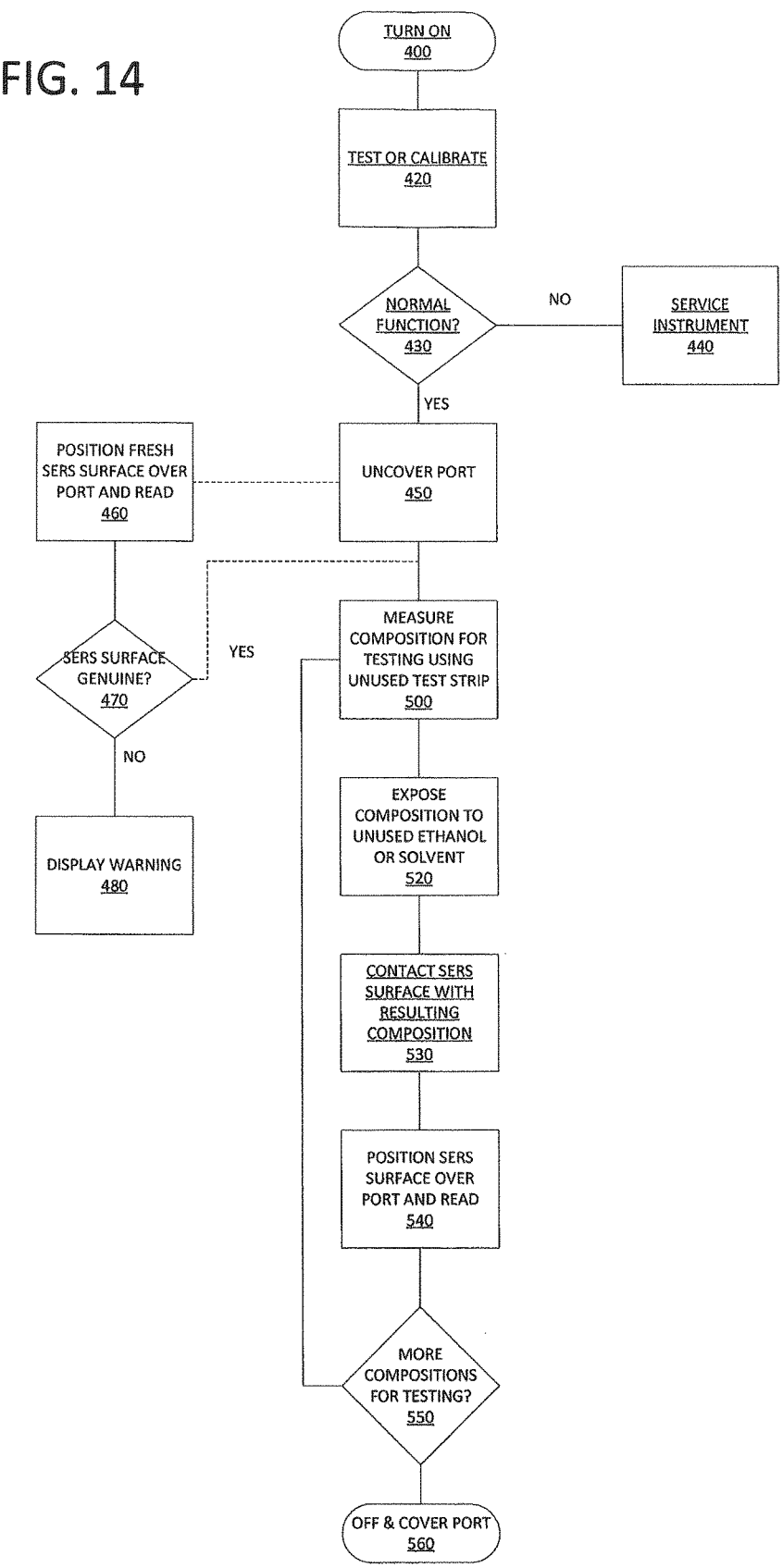
FIG. 14 is a flowchart illustrating a method of the present invention.

An apparatus or kit of the present invention may be used in a method of the present invention, such as that shown in the flowchart of FIG. 14. When a suspect or other source of suspected heroin is identified, spectrometer 10 may be turned on (400). Spectrometer 10, when first turned on and may then perform a self-test or calibration (420) which includes illuminating the inside surface of cover 50 and processor 180 evaluating the resulting spectrum. If signal processor 180 determines that the resulting spectrum does not match the expected spectrum (450) within some predetermined tolerance or parameter, then display 20 presents a message to the user that the instrument should be serviced (444). If the spectrometer 16 is determined (430) by processor 180 to be functioning normally then this is indicated to the user on display 20 and the user may then pivot cover 50 to uncover port 42. The user may then select using display 20 and controls 30, a test to be performed from various possible tests, such as selecting a test for identifying heroin in a sample.

At this point an optional verification sub-routine (460-480) allows the user to place a fresh SERS surface 220 in position over port 42 (460) to be illuminated with laser light and the resulting Raman spectrum collected. If processor 180 determines (470) that the Raman spectrum does not match that of a SERS surface suitable for detecting heroin, or matches a surface that is authorized to be used with spectrometer 16 for the selected test, or the surface appears contaminated, a warning is displayed (480) on display 480 that the SERS surface or test strip 200 is not suitable or not authorized for the selected test. The matching determination may be based on any preselected criteria of the expected SERS surface Raman spectra compared to that of the checked SERS surface Raman spectra. If processor determines the SERS surface is suitable or is authorized for the selected test, or if optional loop (460-480) is omitted, then depression 230 on strip 200 is used to approximately measure (500) an amount of the composition for testing simply by approximately filling depression 230.

The composition in depression 230 is then exposed (520) to the previously unused solvent in vial 300 (the cap of which has been previously removed) simply by placing end 228 into the solvent and stirring or pouring the contents of depression into vial 300. SERS surface 220 is then contacted with the resulting composition simply by placing end 210 of strip 200 into the vial with optional stirring. Typically, at least some small proportion of the sample will dissolve in the solvent.

Figure 7:
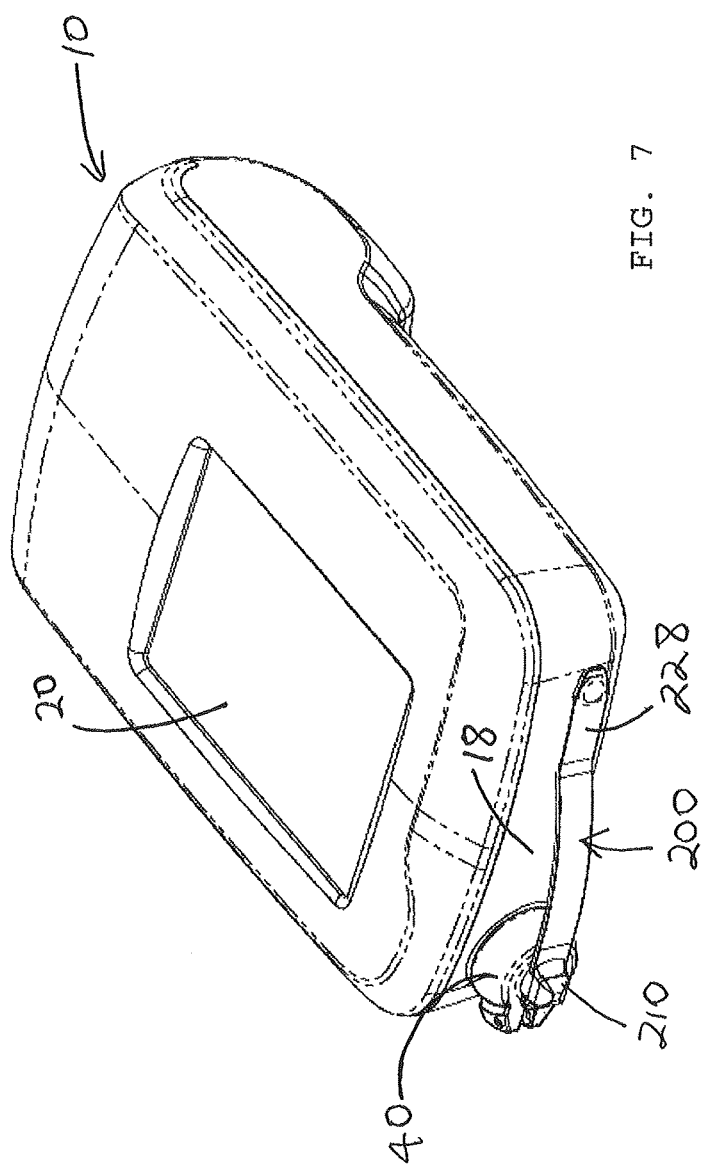
FIG. 7 is a perspective view illustrating use of the SERS test strip of FIG. 5 with the Raman spectrometer of FIGS. 1-5.

Strip 540 is then removed from vial 300 and surface 220 optionally allowed to partially or completely dry in the ambient atmosphere. End 210 of strip 200 is then placed over port 42 as illustrated in FIG. 7 (where controls 30 have been omitted for simplicity) and controls 30 used to activate the laser light for spectrometer 16 to collect the Raman spectrum from the surface 220. Note how strip 200 is dimensioned such that when end 210 is positioned with surface 220 covering port 42, flat section 228 is flat against a flat surface of hand-held spectrometer 10. This assists a user hold strip 200 in position with surface 200 over port 42. Depression in end 210 fits snugly over the end of nose cone 40 when surface 220 is adjacent port 42, and this also assists a user in holding surface 220 in position over port 42. Processor 180 then compares one or more characteristics of the collected Raman spectrum with those in memory for heroin, and identifies the presence or not of heroin in the tested sample composition based on one or more predetermined requirements. The result of the identification is then presented to a user on display 20, and may include an indication of a positive identification, a negative identification, or in some cases that an identification cannot be made.

If more compositions are to be tested (550) steps 500-540 can be repeated, each time using a previously unused strip 200. When no more compositions are to be tested (550), cover 50 can then be swung back to its position covering port 42 and the instrument either turned off manually (560) through controls 30 or shut down automatically by processor 180.

The beneficial effect of using a SERS surface in combination with the appropriate solvent, with a hand-held spectrometer, to identify the presence of heroin in an impure heroin composition can be seen from FIGS. 8-13. In all of FIG. 8-13 a 785 nm laser was used for illumination and when a surface is referenced, the same SERS surface was used as described in connection with surface 220. Note that "substrate" as used in FIGS. 8-13 means a continuous SERS surface as described in connection with surface 220.

Figure 8:
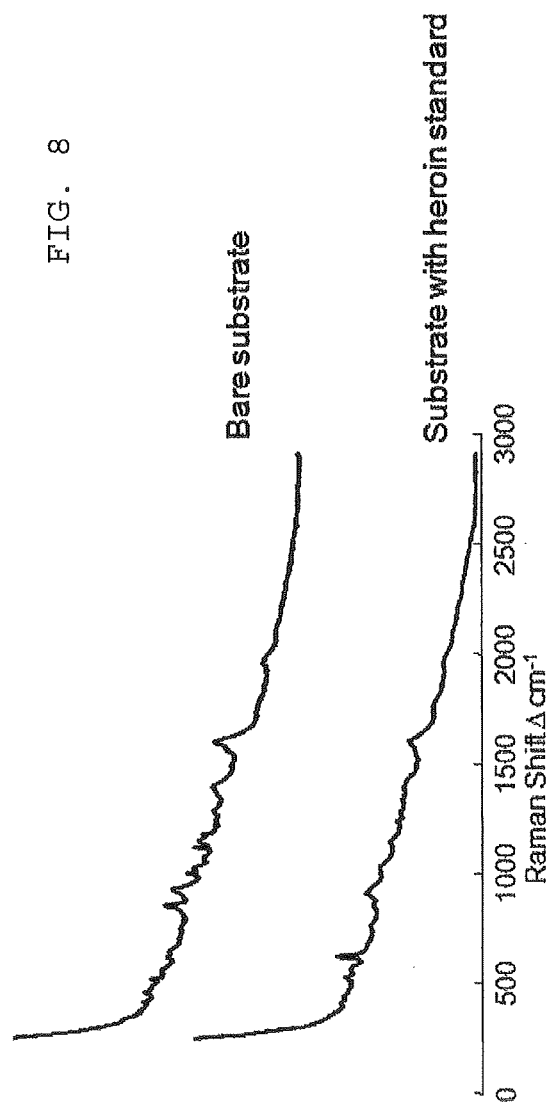
FIG. 8 is a spectra of a bare SERS substrate and the same substrate with a heroin standard—showing the main 625 cm-1 band.
Figure 9:
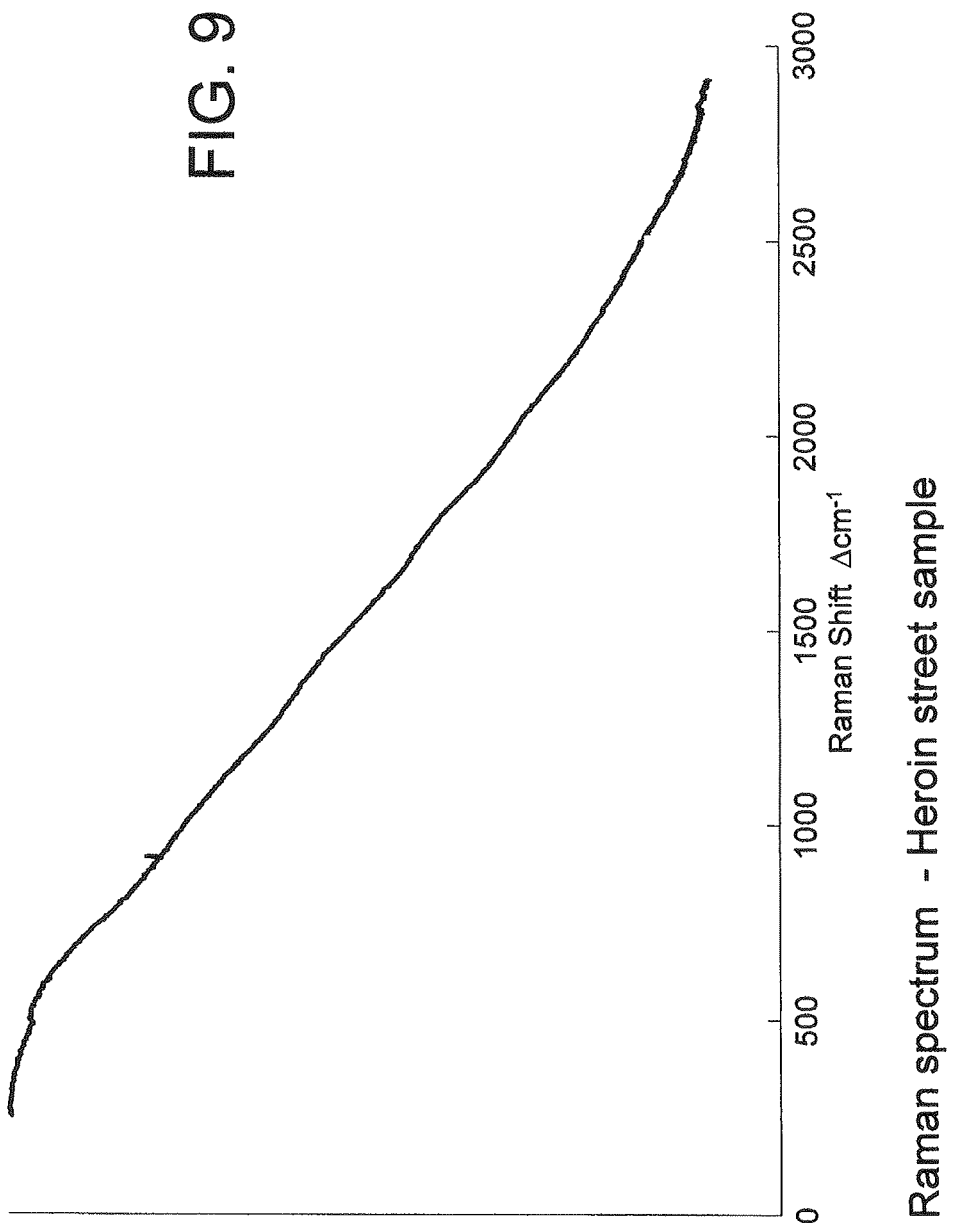
FIG. 9 is a Raman plot of conventional (no SERS) 785 nm backscattered measurement (Raman spectra) of a neat street heroin sample (which contains fluorescent contaminants), no solvent, with measurement being made on powder through a plastic bag
Figure 10:
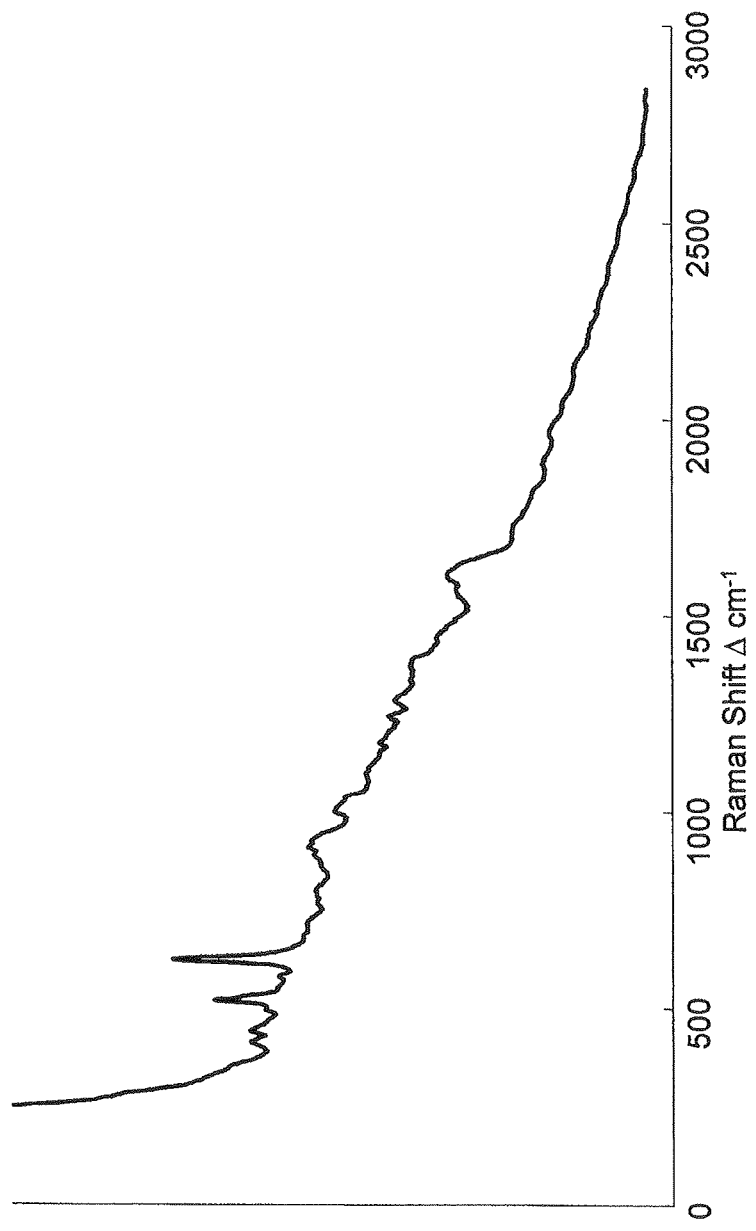
FIG. 10 is a Raman plot of a heroin base standard (a Sigma Aldrich standard, >98% heroin) (no fluorescent contaminants or HCl salt) on a SERS substrate obtained according to a method of the present invention using ethanol.
Figure 11:
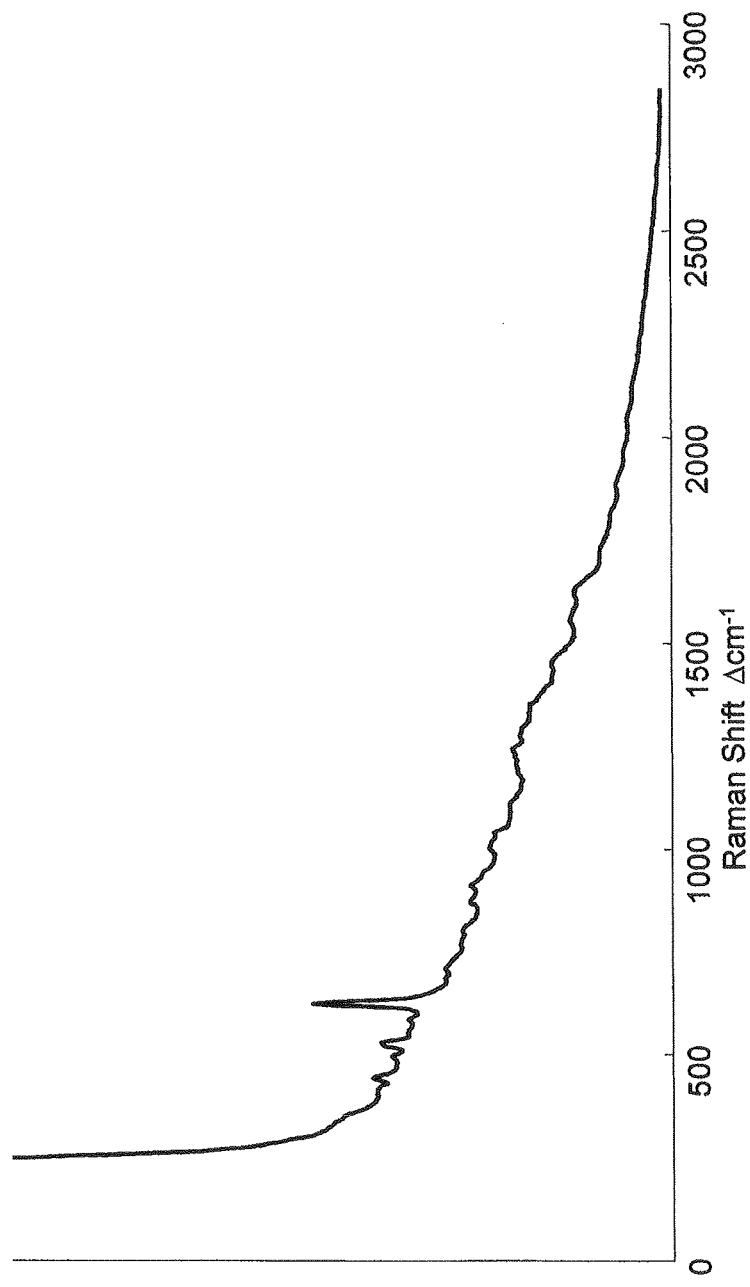
FIG. 11 is a Raman plot obtained under the same conditions as FIG. 10 except using heroin HCl standard.

FIG. 8 then shows the Raman spectrum for a bare SERS surface (top plot) and the characteristic heroin band centered at 625 $cm^{-1}$ is absent. This spectrum though, could be used to identify the surface as appropriate for a heroin test on a particular spectrometer or authorized for use in a heroin test with a particular spectrometer, as described above in connection with optional verification sub-routine 460-480. On the other hand, the substrate with pure heroin standard (bottom plot) clearly shows the characteristic heroin band at 625 $cm^{-1}$. FIG. 9, on the other hand, illustrates the Raman spectrum for a street sample of heroin, with no solvent, measurement made on the powder through a plastic bag. By "street sample", or "street heroin" or the like terms is referenced a typical heroin composition that may be purchased from a dealer of illegal narcotics. Such heroin compositions are typically impure and contain one or more fluorescent components as previously described, which interfere with a Raman signal from the heroin (pure form). In FIG. 9, the fluorescence from such impurities has completely masked the characteristic heroin Raman signal at 625 $cm^{-1}$. FIGS. 10 and 11 illustrate that the characteristic heroin signal from pure free base heroin or the HCl salt, centered around 625 $cm^{-1}$, can still be clearly detected on the SERS surface.

Figure 12:
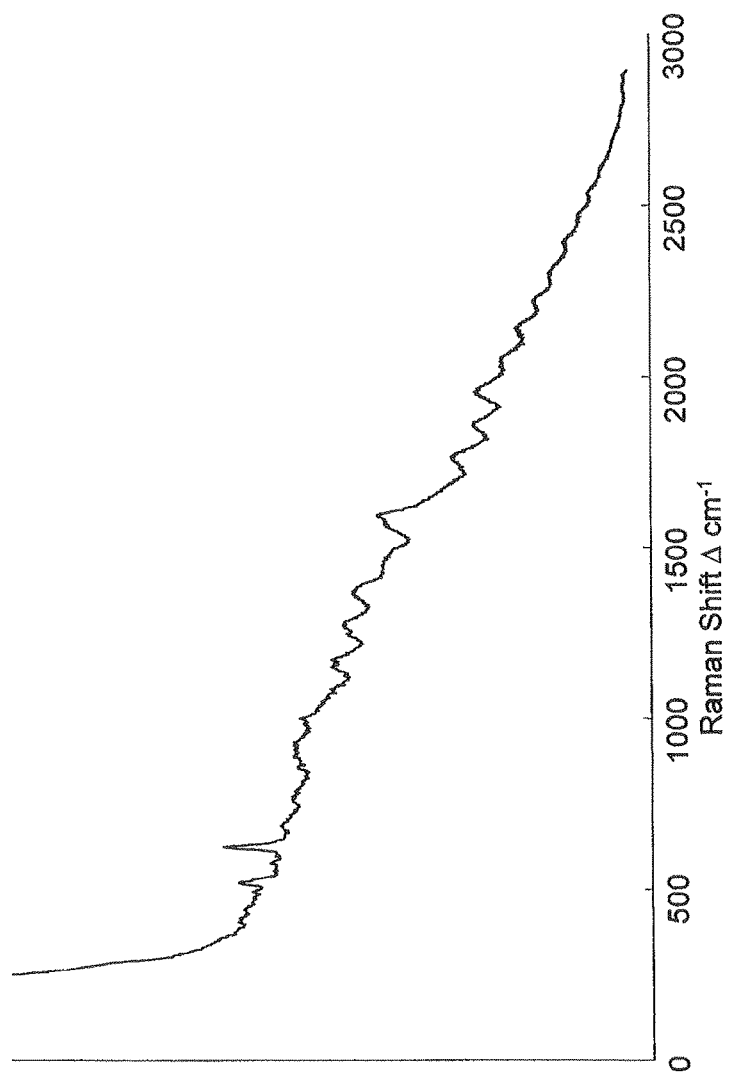
FIG. 12 is a Raman plot of a street heroin sample after contact with methanol and the resulting composition then contacted with the same SERS substrate as in FIG. 10.
Figure 13:
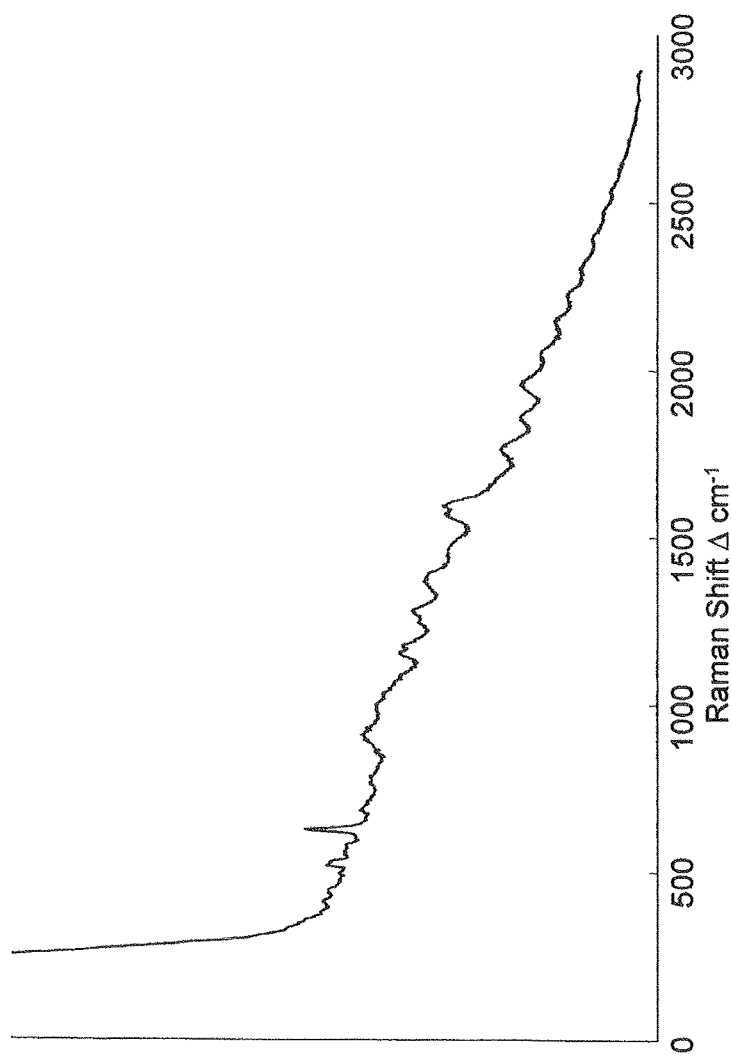
FIG. 13 is the same as FIG. 12 under the same conditions and with the same street heroin sample except ethanol was used instead of methanol. Note the main heroin 625 cm-1 band in FIGS. 10-13.

It is clear from FIG. 9 that it would be impossible to identify the presence of heroin in the street sample by conventional Raman spectroscopy while in the field and using a hand-held conventional Raman spectrometer. FIG. 12, on the other hand, shows the Raman spectrum when the street heroin sample is exposed to methanol and the resulting composition is applied to a surface such as surface 220 in the manner described in detail above and according to the present invention. As can be seen from FIG. 12 the use of a method and apparatus of the present invention has allowed the characteristic heroin peak centered around 625 $cm^{-1}$ to again be detectable. This despite the presence of strongly fluorescent contaminants. FIG. 13 illustrates a similar effect as in FIG. 12. For FIG. 13 the same conditions were used except the solvent was ethanol. Thus, methods and apparatus of the present invention have allowed heroin to be detected even in the presence of one or more strongly fluorescent contaminants which otherwise would completely mask such heroin signal in a conventional Raman spectrum.

Particular embodiments of the present invention have been described in detail above. However, it will be apparent that variations and modifications of the described embodiments are possible. For example, it will be appreciated that operations in the methods described can be performed in the order described or in any other order that is logically possible. In one such variation steps 500, 520 in FIG. 14 could be performed, for example, before step 400 or at some other time before step 530. Accordingly, the present invention is not limited by the embodiments described.

The invention claimed is:

1. A Raman spectrometer comprising:
   (a) a light source to direct light to a SERS surface;
   (b) a spectrograph to acquire a Raman spectrum from the SERS surface; and
   (c) a processor which compares a Raman spectrum of the SERS surface without the presence of a composition thereon, the composition including heroin and at least monoacetyl morphine fluorescent contaminant which interferes with a Raman signal from the heroin, the processor comparing the Raman spectrum with one or more criteria in a memory and identifies the SERS surface as one which is or is not suitable for testing for the presence of heroin, and which also compares the Raman spectrum of the SERS surface with the composition thereon to be tested for heroin with one or more criteria in a memory to test for the presence of heroin.

2. A Raman spectrometer according to claim 1 wherein the processor additionally provides an indication to a user that the SERS surface is or is not suitable for testing for the presence of heroin.

3. A Raman spectrometer according to claim 1 wherein the composition contains between 5 to 95 weight % of the fluorescent contaminant.

4. A Raman spectrometer according to claim 1 wherein the SERS surface comprises gold, silver or copper.

5. A Raman spectrometer according to claim 4 wherein the SERS surface is textured.

6. A Raman spectrometer according to claim 5 wherein the SERS surface is an exposed surface of a silver layer which overlays a silicon substrate.

7. A Raman spectrometer according to claim 6 wherein the silicon substrate is textured.

8. A Raman spectrometer according to claim 1 wherein the spectrometer can acquire a Raman spectrum in a range of between 500 $cm^{-1}$ and 2000 $cm^{-1}$.

9. A Raman spectrometer according to claim 8 wherein the spectrometer can acquire a Raman spectrum in a range of between 600 $cm^{-1}$ and 650 $cm^{-1}$.

10. A method of verifying a SERS surface as suitable for use in enhancing the identification of heroin in a test of a composition including the heroin and at least monoacetyl morphine fluorescent contaminant which interferes with a Raman signal from the heroin on a Raman spectrometer, the method comprising:
    (d) subjecting the SERS surface to a measurement on the Raman spectrometer without the presence of the composition on the SERS surface, and collecting a result of the test;
    (e) comparing, in a processor, the collected result with one or more predetermined criteria stored in a memory; and
    (f) if the collected result meets the one or more predetermined criteria, then subjecting the SERS surface to the test on the Raman spectrometer after exposure of the SERS surface to the composition.

11. A method according to claim 10 wherein the composition contains between 5 to 95 weight % of the fluorescent contaminant.

12. A method according to claim 10 wherein the SERS surface comprises gold, silver or copper.

13. A method according to claim 12 wherein the SERS surface is textured.

14. A method according to claim 13 wherein the SERS surface is an exposed surface of a silver layer which overlays a silicon substrate.

15. A method according to claim 14 wherein the silicon substrate is textured.

16. A method according to claim 10 wherein the Raman signal from the heroin is detected using a wavelength in a range of between 500 $cm^{-1}$ and 2000 $cm^{-1}$.

17. A method according to claim 16 wherein the resulting Raman signal from the heroin is detected using a wavelength in a range of between 600 $cm^{-1}$ and 650 $cm^{-1}$.

18. A Raman spectrometer comprising:
    a light source to direct light to a surface;
    a spectrograph to acquire a Raman spectrum from the surface;
    a processor which compares a Raman spectrum of the surface without the presence of a component thereon, with one or more criteria in a memory and identifies the surface as one which is or is not suitable for testing for the presence of the component, and which also compares the Raman spectrum of the surface with a composition thereon to be tested for the component with one or more criteria in a memory to test for the presence of the component.

19. A Raman spectrometer according to claim 18 wherein the processor identifies the surface as one which is authorized to be used with the spectrometer.

20. A Raman spectrometer according to claim 18 wherein the processor additionally provides an indication to a user that the surface is or is not suitable for testing the presence of the component.

21. A Raman spectrometer according to claim 18 wherein the spectrometer can acquire a Raman spectrum between 500-2000 cm'.

22. A Raman spectrometer according to claim 18 wherein the surface is a SERS surface.

23. A method of verifying a surface as suitable for use in enhancing the identification of a component in a test of a composition for the component on an analytical instrument, comprising:
    subjecting the surface to a measurement on the analytical instrument without the presence of the component on the surface, and collecting a result of the test;
    comparing, in a processor, the collected result with one or more predetermined criteria stored in a memory; and
    if the collected result meets the one or more predetermined criteria, then subjecting the surface to the test on the analytical instrument after exposure to the composition.

24. A method according to claim 23 wherein the surface is verified for use as a SERS surface in a test for identifying the presence of heroin, and the analytical instrument is a Raman spectrometer.

25. A computer program product carrying a computer program which, when loaded into a programmable processor, executes the method of:
    controlling a Raman spectrometer to illuminate a surface without the presence of a component to be tested thereon;
    receiving the Raman spectrum from the surface;
    comparing the Raman spectrum of the surface without the presence of the component thereon, with one or more criteria in a memory and identifying the surface as one which is or is not suitable for testing the presence of the component;

controlling the Raman spectrometer to illuminate the surface with a composition thereon to be tested for the presence of the component; and comparing the Raman spectrum of the surface with the composition thereon with one or more criteria in a memory to test for the presence of the component.

26. The computer program product according to claim 25 wherein identifying the surface as one which is or is not suitable for testing the presence of the component includes identifying the surface as one which is authorized to be used with the spectrometer.

27. The computer program product according to claim 25 further including providing an indication to a user that the surface is one which is or is not suitable for testing the presence of the component.

* * * * *

UNITED STATES PATENT AND TRADEMARK OFFICE
CERTIFICATE OF CORRECTION

PATENT NO. : 10,001,443 B2
APPLICATION NO. : 14/996725
DATED : June 19, 2018
INVENTOR(S) : Craig Morris Gardner et al.

Page 1 of 1

It is certified that error appears in the above-identified patent and that said Letters Patent is hereby corrected as shown below:

In the Claims

Claim 10, Column 11, Line 55:
Replace "(d)"
With "(a)"

Claim 10, Column 11, Line 59:
Replace "(e)"
With "(b)"

Claim 10, Column 11, Line 61:
Replace "(f)"
With "(c)"

Claim 21, Column 12, Line 39:
Replace "500-2000 cm"
With "500-2000 $cm^{-1}$"

Signed and Sealed this
Seventeenth Day of September, 2019

Andrei Iancu
*Director of the United States Patent and Trademark Office*